United States Patent
Hasuda et al.

(10) Patent No.: US 9,885,639 B2
(45) Date of Patent: Feb. 6, 2018

(54) SAMPLE CARRYING DEVICE AND VACUUM APPARATUS

(71) Applicant: HITACHI HIGH-TECH SCIENCE CORPORATION, Minato-ku, Tokyo (JP)

(72) Inventors: Masakatsu Hasuda, Tokyo (JP); Toshiyuki Iwahori, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 0 days.

(21) Appl. No.: 15/005,109

(22) Filed: Jan. 25, 2016

(65) Prior Publication Data

US 2016/0223434 A1 Aug. 4, 2016

(30) Foreign Application Priority Data

Jan. 30, 2015 (JP) .................................. 2015-017440

(51) Int. Cl.
| | | |
|---|---|---|
| *H01J 37/18* | (2006.01) | |
| *G01N 1/14* | (2006.01) | |
| *H01J 37/20* | (2006.01) | |

(52) U.S. Cl.
CPC ................ *G01N 1/14* (2013.01); *H01J 37/20* (2013.01); *H01J 2237/202* (2013.01); *H01J 2237/31745* (2013.01)

(58) Field of Classification Search
CPC ...... G01N 1/14; H01J 37/20; H01J 2237/202; H01J 2237/31745

(Continued)

(56) References Cited

U.S. PATENT DOCUMENTS

| | | | | |
|---|---|---|---|---|
| 3,967,127 A | * | 6/1976 | Rendina .................. | H01J 37/18 250/441.11 |
| 5,529,671 A | * | 6/1996 | Debley ................. | C23C 14/022 204/192.11 |

(Continued)

FOREIGN PATENT DOCUMENTS

| | | | | |
|---|---|---|---|---|
| JP | 2002056796 A | * | 2/2002 | |
| JP | 2006100038 | | 4/2006 | |

(Continued)

OTHER PUBLICATIONS

Translation of JP 2009048802, Hirofumi.*
European Search Report dated Jun. 6, 2016 in Application No. EP 16 15 3209.

*Primary Examiner* — Lisa Caputo
*Assistant Examiner* — Nathaniel T Woodward
(74) *Attorney, Agent, or Firm* — Klintworth & Rozenblat IP LLP; Bruce L. Adams (57) ABSTRACT

A sample carrying device includes a sample carrying rod that carries a sample in the left-right direction in a sample compartment and a preparatory sample compartment, a support body that supports the sample carrying rod, a case that supports the support body such that the support body can rotate around a rotational axis perpendicular to the left-right direction, and an Q-ring disposed between the support body and the case for sealing the sample compartment and the preparatory sample compartment. The sample carrying rod can be switched between a use state where it can carry a sample and a stowed state where it has been moved in the up-down direction from the use state by rotation of the support body. The sample carrying device can easily stow a sample carrying rod in a small space.

20 Claims, 7 Drawing Sheets (58) Field of Classification Search
USPC ....... 73/864.35; 250/442.11, 441.11, 440.11, 250/492.1, 492.21
See application file for complete search history.

(56) References Cited

U.S. PATENT DOCUMENTS

| | | | |
|---|---|---|---|
| 7,777,203 B2* | 8/2010 | Relleen | H01L 21/67213 118/716 |
| 8,816,299 B1* | 8/2014 | Buonodono | H01L 21/68 250/442.11 |
| 2003/0197133 A1* | 10/2003 | Turner | H01J 37/20 250/492.21 |
| 2004/0108067 A1* | 6/2004 | Fischione | G01N 1/32 156/345.38 |
| 2005/0173655 A1* | 8/2005 | Naylor-Smith | H01J 37/3171 250/492.21 |
| 2006/0027763 A1* | 2/2006 | Deak, IV | H01L 21/67069 250/492.21 |

FOREIGN PATENT DOCUMENTS

| | | | |
|---|---|---|---|
| JP | 2009048802 | | 3/2009 |
| JP | 2009048802 A | * | 3/2009 |

* cited by examiner

SAMPLE CARRYING DEVICE AND VACUUM APPARATUS

CROSS REFERENCE TO RELATED APPLICATION(S)

This application claims the benefit of Japanese Patent Application No. 2015-017440, filed Jan. 30, 2015, which is hereby incorporated by reference in its entirety into this application.

BACKGROUND OF THE INVENTION

1. Technical Field

The present invention relates generally to a sample carrying device and a vacuum apparatus.

2. Description of the Related Art

In vacuum apparatuses such as scanning electron microscope or an FIB (Focused Ion Beam) system, a sample carrying rod is used to carry a sample from a preparatory chamber to a sample stage in a sample chamber. Such a sample carrying rod is required to be long enough for carrying a sample from a preparatory chamber to a sample stage, and protrudes from the preparatory chamber when it does not carry a sample. Accordingly, a worker may come in contact with the sample carrying rod protruding out of the preparatory chamber.

Therefore, various sample carrying devices that can stow a sample carrying rod when it does not carry a sample have been proposed. For example, a sample carrying device that includes a rotary unit integrally formed with a sample carrying rod at an end of a preparatory discharge chamber and rotates the rotary unit at a predetermined angle such that the sample carrying rod is positioned in a predetermine direction, up/down and left/right from the sample carrying direction has been proposed in Patent Document 1. According to the sample carrying device disclosed in Patent Document 1, the sample carrying rod does not protrude to be a hindrance.

DOCUMENTS OF RELATED ART (Patent Document 1) Japanese Patent Application Publication No. 2009-48802

SUMMARY OF THE INVENTION

However, in the sample carrying device disclosed in Patent Document 1, the rotary shaft of the rotary unit is inclined with respect to the sample carrying direction. The sample carrying rod is moved along a side of a cone around the rotary shaft of the rotary unit, so a large space is required around the vacuum apparatus. Further, when the sample carrying rod is stowed by rotating the rotary unit, the movement path of the sample carrying rod makes a curved surface, so it cannot be easily stowed, as compared with a sample carrying rod making a planar movement path. Accordingly, the sample carrying devices of vacuum apparatuses of the related art need to be improved to easily stow a sample carrying rod in a small space.

Accordingly, the present invention has been made keeping in mind the above problems occurring in the prior art, and an object of the present invention is to provide a sample carrying device that can easily stow a sample carrying rod in a small space and a vacuum apparatus having the sample carrying device.

In order to accomplish the above object, the present invention provides a sample carrying device including: a sample carrying rod carrying a sample in a predetermined direction in a vacuum chamber; a support body supporting the sample carrying rod; a case supporting the support body such that the support body can rotate around a rotational axis perpendicular to the predetermined direction; and a seal disposed between the support body and the case and sealing the vacuum chamber, in which the sample carrying rod can be switched between a use state where the sample carrying rod can carry the sample and a stowed state where the sample carrying rod has been moved to a predetermined position from the use stage by rotation of the support body.

According to the present invention, since the sample carrying rod can be rotated by the support body and the case with the seal therebetween, it is possible to stow the sample carrying rod with the vacuum chamber in a vacuum stage, when it does not carry a sample. Further, since the rotational axis is perpendicular to a predetermined direction in which a sample is carried, the sample carrying rod is turned in a plane perpendicular to the rotational axis. Accordingly, as compared with when a rotational axis is inclined with respect to a sample-carrying direction, it is possible to reduce the space for stowing the sample carrying rod. Further, since the sample carrying rod is moved in a plane, it can be easily stowed. Therefore, it is possible to achieve a sample carrying device that can easily stow a sample carrying rod in a small space.

The sample carrying device may further include a holding mechanism keeping the sample carrying rod in the stowed state.

When the vacuum chamber is in a vacuum stage, negative pressure is applied to the sample carrying rod. Accordingly, a force that pulls the sample carrying rod into the vacuum chamber is applied to the sample carrying rod. According to the present invention, since the sample carrying device includes the holding mechanism for keeping the sample carrying rod stowed, it is possible to prevent the sample carrying rod from being pulled into the vacuum chamber by the negative pressure.

The holding mechanism may include a coupler formed at a first end of the sample carrying rod and a recess formed on the inner side of the case to be coupled to the coupler in the stowed state.

According to the present invention, since the holding mechanism is composed of a coupler such as a male thread formed at a first end of the sample carrying rod and a recess such as a female thread formed on the inner side of the case, it is possible to keep the sample carrying rod stowed with a simple configuration.

On outer sides of the case, a slit may be formed in a plane perpendicular to the rotational axis to receive the sample carrying rod and a cut-portion may be formed across the slit as the holding mechanism.

According to the present invention, since the cut-portion is formed across the slit on the outer side of the case, it is possible to prevent the sample carrying rod from moving in the slit by fixing the sample carrying rod in the cut-portion. Accordingly, it is possible to keep the sample carrying rod stowed with a simple configuration.

In the sample carrying device, the support body may be formed in a spherical shape.

According to the present invention, since the support body is formed in a spherical shape, the support body can be supported rotatably with respect to the case and the sealing can be easily achieved by the seal between the support body and the case.

A vacuum apparatus of the present invention includes the sample carrying device.

According to the present invention, since the sample carrying device is included, it is possible to achieve a vacuum apparatus that can easily stow the sample carrying rod in a small space.

According to the present invention, since the sample carrying rod can be rotated by the support body and the case with the seal therebetween, it is possible to stow the sample carrying rod with the vacuum chamber in a vacuum stage, when it does not carry a sample. Further, since the rotational axis is perpendicular to a predetermined direction in which a sample is carried, the sample carrying rod is turned in a plane perpendicular to the rotational axis. Accordingly, as compared with when a rotational axis is inclined with respect to a sample-carrying direction, it is possible to reduce the space for stowing the sample carrying rod. Further, since the sample carrying rod is moved in a plane, it can be easily stowed. Therefore, it is possible to achieve a sample carrying device that can easily stow a sample carrying rod in a small space.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Hereinafter, embodiments of the present invention are described with reference to drawings.

First Embodiment

First, a vacuum apparatus 1 according to a first embodiment is described. In this embodiment, a focused ion beam system is exemplified as the vacuum apparatus 1.

Figure 1:
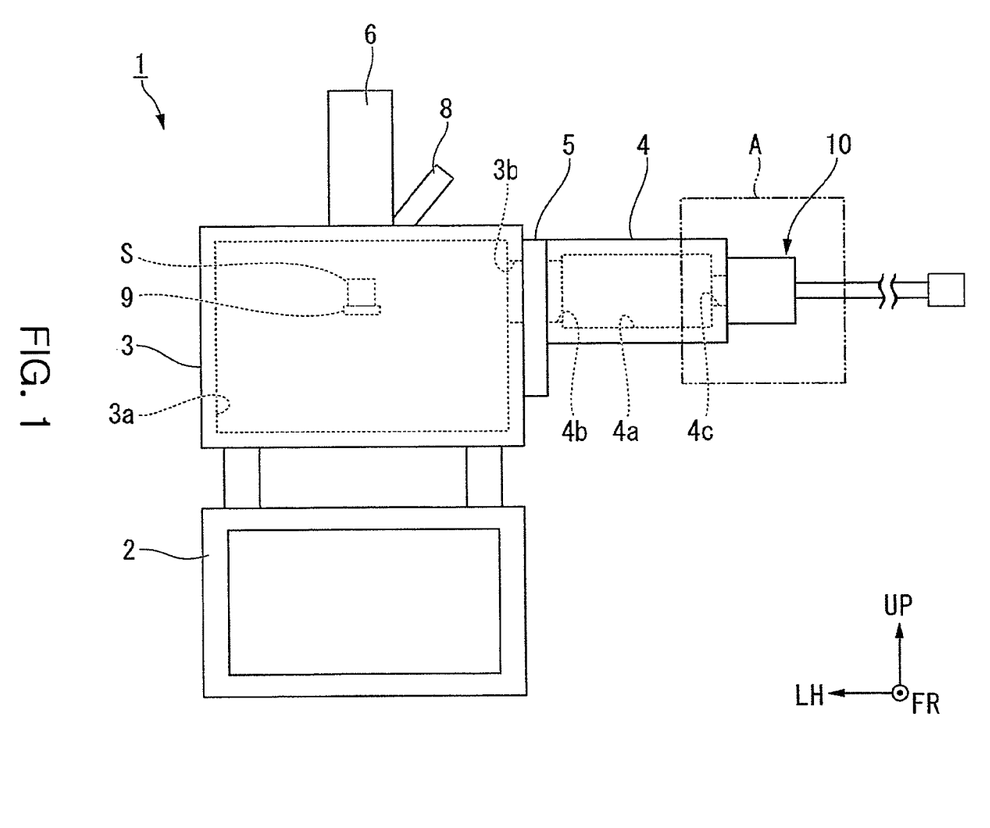
FIG. 1 is a diagram illustrating the configuration of a vacuum apparatus according to a first embodiment of the present invention.

FIG. 1 is a diagram illustrating the configuration of a vacuum apparatus according to a first embodiment of the present invention. The vacuum apparatus 1 is placed on a horizontal surface in use. In the drawings, the vertical direction is indicated by an arrow UP, the front direction is indicated by an arrow FR, and the left direction is indicated by an arrow LH.

As shown in FIG. 1, the vacuum apparatus 1 includes a first vacuum chamber 3, a second vacuum chamber 4, and a sample carrying device 10. The vacuum device 1 is placed on an anti-vibration bed 2.

The first vacuum chamber 3 is, for example, made of metal in the shape of a hollow hexahedron and has a sample compartment 3a. A sample stage (not shown) is in the sample compartment 3a. A sample holder 9 with a sample S fixed thereto can be set on the sample stage. A hole 3b is formed in the left-right direction through the right side of the first vacuum chamber 3.

A first exhaust pump (not shown) is connected to the first vacuum chamber 3. The first exhaust pump makes the sample compartment 3a in a vacuum state by reducing the pressure in the sample compartment 3a. An ion beam barrel 6 and a detector 8 are disposed on the first vacuum pump 3. The ion beam barrel 6 can radiate an ion beam toward a sample S set on the sample stage. The detector 8 includes a secondary electron detector that detects secondary electrons that are produced from the sample S when an ion beam is radiated to the sample S.

The second vacuum chamber 4 is coupled to the right side of the first vacuum chamber 3 through a gate valve 5. The second vacuum chamber 4 is, for example, made of metal in the shape of a hollow hexahedron and has a preparatory sample compartment 4a. The preparatory sample compartment 4a has a volume sufficiently smaller than the volume of the sample compartment 3a. A first hole 4b is formed in the left-right direction through the left side of the second vacuum chamber 4 to be aligned with the hole 3b of the first vacuum chamber 3 in the left-right direction. When the gate valve 5 is open, the sample compartment 3a and the preparatory sample compartment 4a communicate with each other through the hole 3b of the first vacuum chamber 3 by the first hole 4b. A second hole 4c is formed in the left-right direction through the right side of the second vacuum chamber 4 to be aligned with the first hole 4b in the left-right direction.

A second exhaust pump (not shown) is connected to the second vacuum chamber 4, similar to the first vacuum chamber 3. The second exhaust pump makes the preparatory sample compartment 4a in a vacuum state by reducing the pressure in the preparatory sample compartment 4a. The second vacuum chamber 4 has a door (not shown) for opening/closing the preparatory sample compartment 4a and the sample S can be replaced in the preparatory sample compartment 4a.

The sample carrying device 10 is described hereafter.

Figure 2:
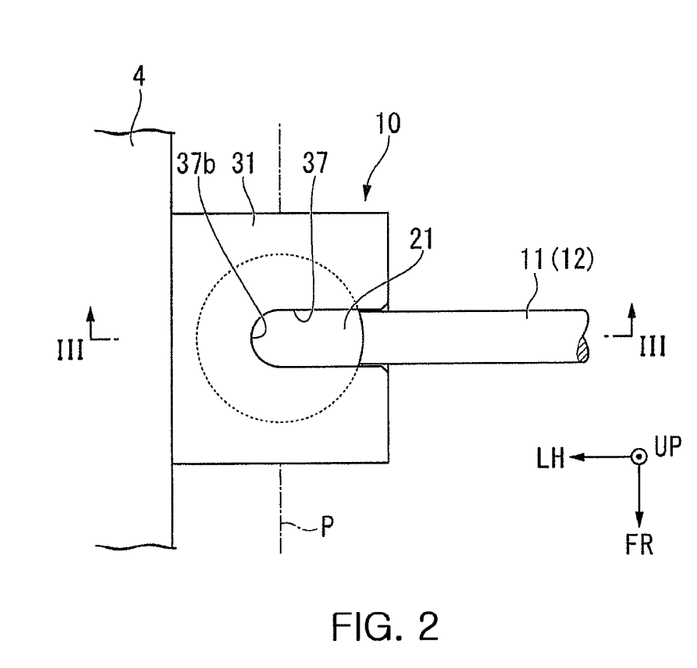
FIG. 2 is a plan view of the portion A of FIG. 1.
Figure 3:
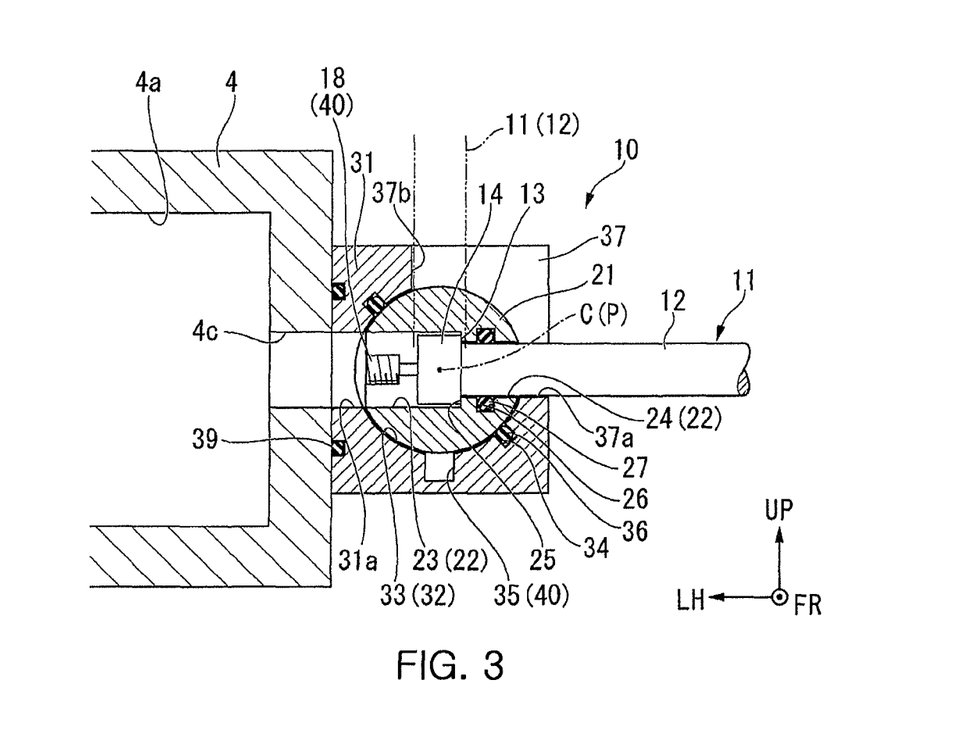
FIG. 3 is a cross-sectional view taken along line of FIG. 2.

FIG. 2 is a plan view of the portion A of FIG. 1. FIG. 3 is a cross-sectional view taken along line III-III of FIG. 2.

As shown in FIG. 3, the sample carrying device 10 is disposed on the right side of the second vacuum chamber 4. The sample carrying device 10 includes a sample carrying rod 11, a support body 21 supporting the sample carrying rod 11, and a case 31 supporting the support body 21.

The sample carrying rod 11 carries a sample S (the sample holder 9) in the left-right direction (corresponding to "predetermined direction" in claims) between the sample compartment 3a and the preparatory sample compartment 4a. The sample carrying rod 11 is, for example, a circular bar made of metal. The sample carrying rod 11 has a body 12 uniformly extending and an enlarging portion 14 increased in diameter by a step 13 from an end of the body 12. A coupler 18 (a male bolt in this embodiment) coupled to a coupling portion (not shown) on the sample holder 9 protrudes at the end of the enlarging portion 14. The coupler 18 is not limited to the male bolt, and for example, it may be a hook that is hooked to the coupling portion of the sample holder 9.

The support body 21 is, for example, made of metal in the shape of a sphere. A hole 22 having a circular cross-section is formed in the support body 21. The central axis of the hole 22 passes the center of the support body 21. A large-diameter portion 23 and a small-diameter portion 24 are coaxially formed with a stepped side 25 therebetween in the hole 22. The large-diameter portion 23 is deeper than the distance from the step 13 to the end of the coupler 18 in the longitudinal direction of the sample carrying rod 11. The inner diameter of the large-diameter portion 23 is larger than the diameter of the enlarging portion 14 of the sample carrying rod 11. The inner diameter of the small-diameter portion 24 is slightly larger than the diameter of the body 12 of the sample carrying rod 11. A groove 26 is circumferentially formed on the inner side of the small-diameter portion 24. A first O-ring 27 is fitted in the groove 26.

The sample carrying rod 11 is inserted in the hole 22 of the support body 21. The body 12 of the sample carrying rod 11 is positioned in the small-diameter portion 24 and the enlarging portion 14 is disposed in the large-diameter portion 23. Accordingly, the step 13 of the sample carrying rod 11 can come in contact with the stepped side 25 of the support body 21 and prevents the sample carrying rod 11 from separating out of the hole 22. The first O-ring 27 is in contact with the bottom of the groove 26 of the support body 21 and the outer side of the body 12 of the sample carrying rod 11. Accordingly, the first O-ring 27 seals the portion between the small-diameter portion 24 of the hole 22 and the body 12 of the sample carrying rod 11.

The case 31 is coupled to the right side of the second vacuum chamber 4 with a second O-ring 39 therebetween. The case 31 is, for example, made of metal in the shape of a hollow hexahedron. A spherical support body seat 33 is formed in the case 31 by a spherical inner side 32. The support body 31 is supported rotatably around the center C of the support body seat 33. The inner diameter of the support body seat 33 is slightly larger than the outer diameter of the support body 21 such that the support body 21 can rotate in the support body seat 33.

A groove 34 is formed on the inner side 32 of the support body seat 33. The groove 34 passes through the center C of the support body seat 33 along a virtual plane rotated at 45° clockwise from the horizontal plane, when seen from the front. A third O-ring 36 (corresponding to a seal in claims) is fitted in the groove 34. The third O-ring 36 is in contact with the outer side of the support body 21 and the inner side 32 of the case 31 and seals the preparatory sample compartment 4a, the sample compartment 3a, and the case 31 that are connected by a hole 31a described below.

A recess 35 (a female-threaded portion in this embodiment) for coupling the coupler 18 of the sample carrying rod 11 is formed under the support body seat 33. The recess 35 overlaps the center C of the support body seat 33 when seen from above.

The hole 31a is formed in the left-right direction through the left side of the case 31. The hole 31a overlaps the center C of the support body seat 33 or the second hole 4c of the second vacuum chamber 4 when seen in the left-right direction. The hole 31a communicates with the preparatory sample compartment 4a through the second hole 4c of the second vacuum chamber 4. The sizes in the left-right direction and the up-down direction of the hole 31a are larger than the diameter of the enlarging portion 14 of the sample carrying rod 11.

Figure 4:
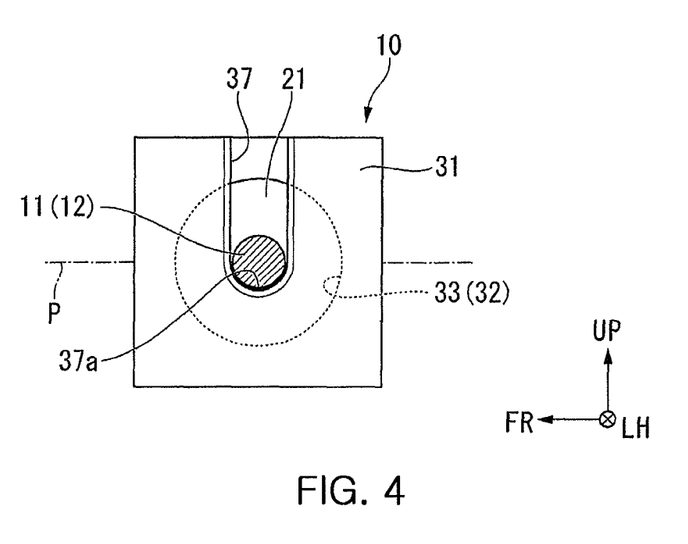
FIG. 4 is a right side view of the portion A of FIG. 1.

FIG. 4 is a right side view of the portion A of FIG. 1.

As shown in FIGS. 2 and 4, a slit 37 is formed on the right side and the top side of the case 31. The body 12 of the sample carrying rod 11 supported by the support body 21 is inserted in the slit 37. The slit 37 is formed from the center of the right side to the center of the top side of the case 31 through center C of the support body seat 33 on a plane perpendicular to the front-rear direction. The width of the silt 37 is slightly larger than the diameter of the body 12 of the sample carrying rod 11 and smaller than the outer diameter of the support body 21.

As shown in FIG. 3, the lower end 37a (the end on the right side of the case 31) of the slit 37 is formed in a U-shape when seen in the left-right direction so that the sample carrying rod 11 can be positioned in the left-right direction. The left end 37b (the end on the top of the case 31) of the slit 37 is formed in a U-shape when seen in the up-down direction so that the sample carrying rod 11 can be positioned in the up-down direction. The sample carrying rod 11 and the support body 21 can rotate around a rotational axis P passing in the front-rear direction through the center C of the support body seat 33. The sample carrying rod 11 can be switched to a position (indicated by a solid line in FIG. 3) where it can carry the sample S (sample holder 9) and a position (corresponding to a 'predetermined position' in claims) (indicated by a two-dot chain line in FIG. 3) where it is moved with rotation of the support body 21 and stowed in the up-down direction.

Operation of the sample carrying device 10 according to this embodiment is described hereafter. Refer to FIGS. 1 and 3 for the reference numerals of components in the following description.

The operation for carrying a sample to replace the sample in the vacuum apparatus 1 is described first. Further, it is assumed that the sample holder 9 holding the sample S is set on the sample stage in the sample compartment 3a in the early stage of replacing the sample.

In order to replace the sample S, the sample carrying rod 11 is moved into the use state in the left-right direction. In the use state, as the sample carrying rod 11 is pushed left, a first end (the enlarging portion 14) of the sample carrying rod 11 is moved through the hole 31a of the case 31 and the second hole 4c of the second vacuum chamber 4. Further, as the sample carrying rod 11 is pushed, the first end of the sample carrying rod 11 is moved through the first hole 4b of the second vacuum chamber 4 and the hole 3b of the first vacuum chamber 3.

After the first end of the sample carrying rod 11 is moved close to the sample stage in the sample compartment 3a, the coupler 18 at the first end of the sample carrying rod 11 is coupled to the coupling portion of the sample holder 9 set on the sample stage by turning the sample carrying rod 11. Next, the sample carrying rod 11 is taken out to the right such that the sample holder 9 is carried into the preparatory sample compartment 4a from the sample stage in the sample compartment 3a, and then the gate valve 5 is closed. Next, with the sample compartment 3a maintained in the vacuum state, the internal pressure of the preparatory compartment 4a is increased to the atmospheric pressure by injecting gas such as air or nitrogen, and then the door of the second vacuum chamber 4 is opened. Accordingly, the sample S held by the sample holder 9 can be replaced.

The sample S held by the sample holder 9 is replaced, and then the door of the second vacuum chamber 4 is closed and the preparatory sample compartment 4a is evacuated by the second exhaust pump. When the vacuum degree of the preparatory sample compartment 4a becomes substantially the same as the vacuum degree of the sample compartment 3a, the gate valve 5 is opened and the sample carrying rod 11 is pushed inside, thereby carrying the sample holder 9 to the sample stage in the sample compartment 3a from the preparatory sample compartment 4a. Next, the coupling portion of the sample holder 9 and the coupler 18 of the sample carrying rod 11 are decoupled by turning the sample carrying rod 11. With the process described above, replacing the sample S is finished.

As described above, since only the preparatory sample compartment 4a smaller in volume than the sample compartment 3a is opened to the atmosphere when a sample is replaced in the vacuum apparatus 1, the time for evacuating the vacuum chamber to replace a sample is reduced.

A process of stowing the sample carrying rod 11 is described hereafter.

Figure 5:
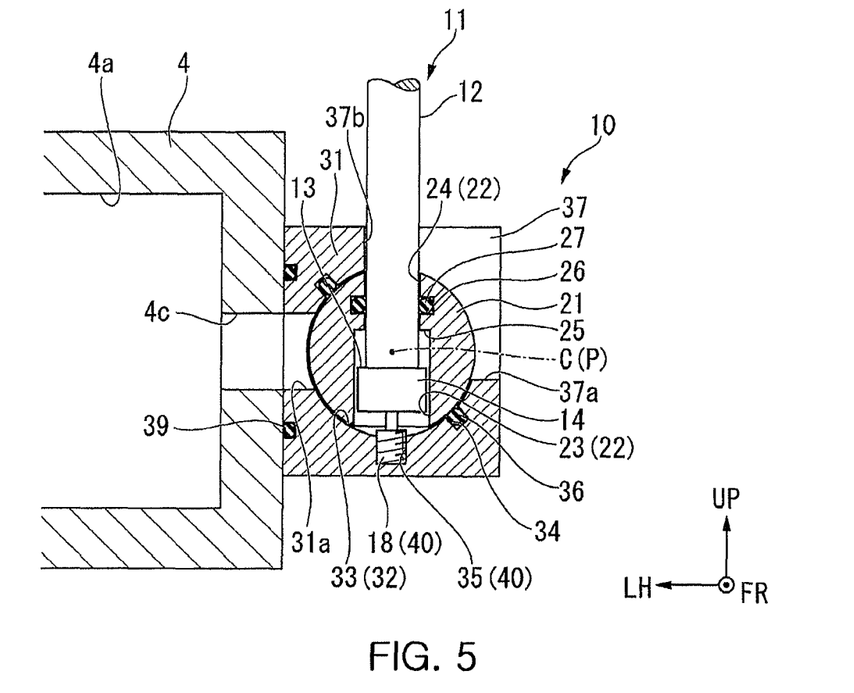
FIG. 5 is a cross-sectional view taken along line of FIG. 2.

FIG. 5 is a cross-sectional view taken along line III-III of FIG. 2. In FIG. 5, the coupler 18 of the sample carrying rod 11 is coupled to the recess 35 of the case 31.

When the sample carrying rod 11 is stowed, the sample carrying rod 11 is taken out and the step 13 is brought in contact with the stepped side 25 of the support body 21. Since the depth of the large-diameter portion 23 is larger than the distance from the step 13 of the sample carrying rod 11 to the first end of the coupler 18, the first end of the sample carrying rod 11 is inserted in the hole 22 of the support body 21. Next, the sample carrying rod 11 is stowed from the use state by turning it counterclockwise at 90° around the rotational axis P when seen from the front. When the sample carrying rod 11 is stowed, the sample carrying rod 11 is pushed down and the coupler 18 at the first end of the sample carrying rod 11 is coupled to the recess 35 of the support body seat 33 (See FIG. 5). Accordingly, the sample carrying rod 11 is turned down to the right, so it is not moved to the use state. In other words, the coupler 18 of the sample carrying rod 11 and the recess 35 of the case 31 function as a holding mechanism 40 that keeps the sample carrying rod 11 stowed. Further, since the sample carrying rod 11 is fixed in the up-down direction, the space occupied by the vacuum apparatus 1 when a sample is not carried can be reduced.

As described above, the sample carrying device 10 of this embodiment includes the sample carrying rod 11 that carries a sample in the left-right direction in the sample compartment 3a and the preparatory sample compartment 4a, the support body 21 that supports the sample carrying rod 11, the case 31 that supports the support body 21 such that the support body 21 can rotate around the rotational axis P perpendicular to the left-right direction, and the third O-ring 36 that is disposed between the support body 21 and the case 31 and seals the sample compartment 3a and the preparatory sample compartment 4a. The sample carrying rod 11 may be switched between the use state where it can carry a sample S and the stowed state where it has been moved in the up-down direction from the use state by rotation of the support body 21.

According to this configuration, since the sample carrying rod 11 can be rotated by the case 31 and the support 21 with the third O-ring 36 therebetween, it is possible to stow the sample carrying rod 11 with the sample compartment 3a and the preparatory sample compartment 4a under a vacuum state when the sample carrying rod 11 does not carry a sample. Further, since the rotational axis P is perpendicular to the left-right direction in which the sample S is carried, the sample carrying rod 11 is turned in the plane perpendicular to the rotational axis P. Accordingly, as compared with when a rotational axis is inclined with respect to a sample-carrying direction, it is possible to reduce the space for stowing the sample carrying rod 11. Further, since the sample carrying rod 11 is moved in a plane, it can be easily stowed.

Further, in the sample carrying device 10, the sample carrying rod 11 is turned and stowed by the support body 21 and the case 31, so it is not required to make the sample carrying rod complicated, for example, forming joints on the sample carrying rod, to stow it. Accordingly, the sample carrying rod 11 may be a simple rod and it is possible to make sure of keeping the sample compartment 3a and the preparatory sample compartment 4a in a vacuum state.

When the preparatory sample compartment 4a is under a vacuum state, negative pressure is applied to the sample carrying rod 11. Accordingly, when the sample carrying rod 11 is in the use state, a force that pulls the sample carrying rod 11 into the preparatory sample compartment 4a is applied to it. Since the sample carrying device 10 of this embodiment has the holding mechanism 40 that keeps the sample carrying rod 11 stowed, the sample carrying rod 11 is prevented from being pulled into the preparatory sample compartment 4a by the force.

Further, since the holding mechanism 40 is composed of the coupler 18 at the first end of the sample carrying rod 11 and the recess 35 on the inner side 32 of the case 31, it is possible to keep the sample carrying rod 11 stowed with a simple configuration.

In particular, in this embodiment, the coupler 18 is used for moving the sample holder 9, it is possible to achieve the holding mechanism 40 only by forming the extra recess 35. Accordingly, it is possible to simplify the configuration of the sample carrying device 10.

Further, the support body 21 has a spherical shape, the support body 21 is rotatably supported with respect to the case 31 and sealing can be easily achieved by the third O-ring 36 between the support body 21 and the case 31.

Further, since the vacuum apparatus 1 of this embodiment includes the sample carrying device 10, it is possible to easily stow the sample carrying rod 11 in a small space.

Second Embodiment

A sample carrying device 110 of the second embodiment is described hereafter.

Figure 6:
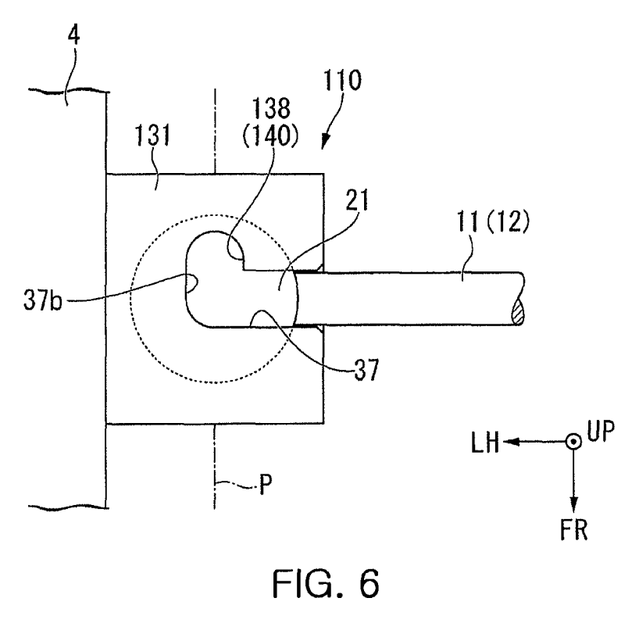
FIG. 6 is a plan view of a portion corresponding to the portion A of FIG. 1, illustrating a sample carrying device according to a second embodiment of the present invention.
Figure 7:
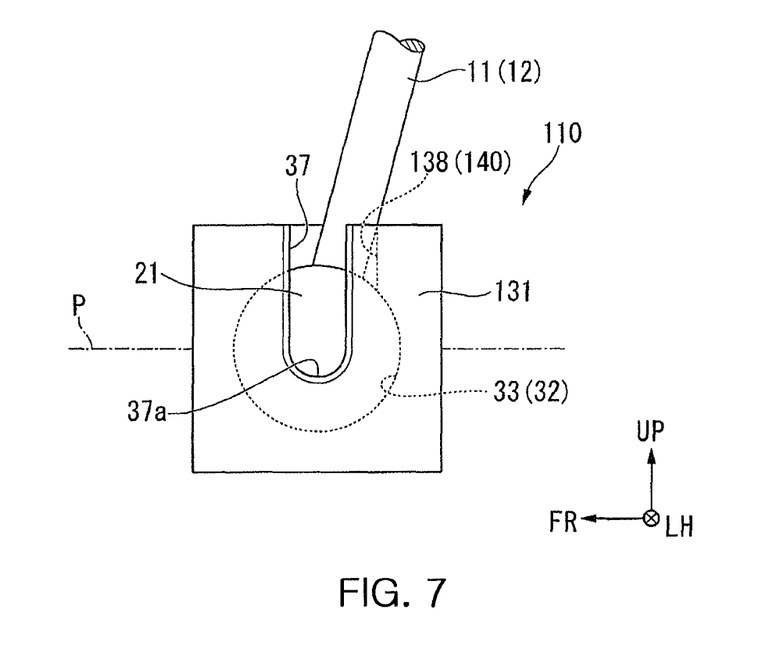
FIG. 7 is a right side view of the portion corresponding to the portion A of FIG. 1, illustrating a sample carrying device according to the second embodiment of the present invention.

FIG. 6 is a plan view of a portion corresponding to the portion A of FIG. 1, illustrating a sample carrying device according to the second embodiment of the present invention. FIG. 7 is a right side view of the portion corresponding to the portion A of FIG. 1, illustrating the sample carrying device according to the second embodiment of the present invention. In FIG. 6, a sample carrying rod 11 is in a use state. In FIG. 7, a sample carrying rod 11 is in a stowed state.

The second embodiment shown in FIG. 6 is different from the first embodiment shown in FIG. 2 in that a cut-portion 138 is formed at the left end 37b of the slit 37. Further, the same components as those in the first embodiment shown in FIG. 1 are given the same reference numerals and not described in detail herein.

As shown in FIG. 6, the cut-portion 138 crossing the slit 37 is formed on the top of the case 131. The cut-portion 138 is formed rearward from the left end 37b of the slit 37. The left-right width of the cut-portion 138 is slightly larger than the diameter of the body 12 of the sample carrying rod 11.

As shown in FIG. 7 the sample carrying rod 11, which has been moved in the up-down direction from the use state, is inserted into the cut-portion 138 by pushing the sample carrying rod 11 down rearward. Accordingly, the sample carrying rod 11 inserted in the cut-portion 138 is maintained therein by its own weight. Accordingly, it prevents the sample carrying rod 11 from being switched into the use stage from the stowed state by turning it down to the right. Further, the cut-portion 138 functions as a holding mechanism 140 that keeps the sample carrying rod 11 stowed.

As described above, the slit 37 in which the sample carrying rod 11 is inserted and the cut-portion 138 formed across the slit 37 as the holding mechanism 140 are formed in the case 131 of the sample carrying device 110 of this embodiment.

According to this configuration, since the cut-portion 138 formed across the slit 37 is formed on the top of the case 31, it is possible to prevent the sample carrying rod 11 from moving in the slit 37 by fixing the sample carrying rod 11 in the cut-portion 138. Accordingly, it is possible to keep the sample carrying rod 11 stowed with a simple configuration.

The present invention is not limited to the embodiments described with reference to the drawings and may be modified in various ways.

For example, although the support body 21 is formed in a spherical shape in the embodiments, it is not limited thereto and may be formed in a long spherical shape.

Further, although the sample carrying rod 11 can be turned at 90° around the rotational axis P, it is not limited thereto. For example, by making the sample carrying rod 11 be rotatable over 90° around the rotational axis P in the left-right direction, it can keep stowed by its own weight.

Further, the case 31 may be made rotated ±90° or 180°, in which the sample carrying rod 11 can be bent left and right or downward, for example, like the operator of a wheelchair.

Although a focused ion beam apparatus is exemplified as the vacuum apparatus in the embodiments, the present invention may be available for a particle beam apparatus, an analysis device such as an auger electron spectrometer or a secondary ion mass spectrometry, a film forming apparatus, and a spatter apparatus, etc. The components in the embodiments may be appropriately replaced with other well-known components without departing from the scope of the present invention.

What is claimed is:

1. A sample carrying device comprising:
a sample carrying rod configured to carry a sample in a predetermined direction in a vacuum chamber;
a support body supporting the sample carrying rod;
a case supporting the support body such that the support body can rotate around a rotational axis perpendicular to the predetermined direction; and
a seal disposed between the support body and the case for sealing the vacuum chamber,
wherein the sample carrying rod can be switched by rotation of the support body between a use state, where the sample carrying rod can carry the sample, and a stowed state, where the sample carrying rod has been moved to a predetermined position from the use state so that a first end of the sample carrying rod is positioned outside the vacuum chamber and inside the support body, and
wherein on outer sides of the case, a slit is formed in a plane perpendicular to the rotational axis to receive the sample carrying rod.

2. The device of claim 1, further comprising a holding mechanism configured to keep the sample carrying rod in the stowed state.

3. The device of claim 2, wherein the holding mechanism includes a coupler provided at the first end of the sample carrying rod, and a recess formed on the inner side of the case and configured to be coupled to the coupler in the stowed state.

4. The device of claim 3, wherein the support body is formed in a spherical shape.

5. A vacuum apparatus comprising the sample carrying device of claim 4.

6. A vacuum apparatus comprising the sample carrying device of claim 3.

7. The device of claim 2, wherein the case includes a cut-portion formed across the slit as the holding mechanism.

8. The device of claim 7, wherein the support body is formed in a spherical shape.

9. A vacuum apparatus comprising the sample carrying device of claim 8.

10. A vacuum apparatus comprising the sample carrying device of claim 7.

11. The device of claim 2, wherein the support body is formed in a spherical shape.

12. A vacuum apparatus comprising the sample carrying device of claim 11.

13. A vacuum apparatus comprising the sample carrying device of claim 2.

14. The device of claim 1, wherein the support body is formed in a spherical shape.

15. A vacuum apparatus comprising the sample carrying device of claim 14.

16. A vacuum apparatus comprising the sample carrying device of claim 1.

17. A sample carrying device, comprising:
a sample carrying rod having a rod end portion configured to carry a sample in a predetermined direction in a vacuum chamber;
a support body slidably supporting the sample carrying rod for sliding movement in the predetermined direction to position the rod end portion inside the vacuum chamber and in an opposite direction, opposite to the predetermined direction, to position the rod end portion inside the support body;
a case configured to rotatably support the support body for rotational movement about a rotational axis perpendicular to the predetermined direction between one position, in which the sample carrying rod is in a use state and can slide in the predetermined direction and the opposite direction, and another position, in which the sample carrying rod is in a stowed state with the rod end portion inside the support body and the sample carrying rod extending upwards; and
a seal disposed between the support body and the case for sealing the vacuum chamber,
wherein on outer sides of the case, a slit is formed in a plane perpendicular to the rotational axis to receive the sample carrying rod.

18. The sample carrying device according to claim 17; further comprising a holding mechanism configured to releasably keep the sample carrying rod in the stowed state.

19. The sample carrying device according to claim 18; wherein the holding mechanism comprises a coupler connected to the rod end portion and configured to couple to a sample holder, and a recess provided on an inner side of the case for receiving therein the coupler.

20. A vacuum apparatus including the sample carrying device of claim 17.

* * * * *